United States Patent
Are et al.

(10) Patent No.: US 11,006,818 B2
(45) Date of Patent: May 18, 2021

(54) PORTABLE LAPAROSCOPE SYSTEM

(71) Applicant: The Board of Regents of the University of Nebraska, Lincoln, NE (US)

(72) Inventors: Chandrakanth Are, Omaha, NE (US); Madhuri Are, Omaha, NE (US); Dennis Alexander, Lincoln, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 516 days.

(21) Appl. No.: 15/886,404

(22) Filed: Feb. 1, 2018

(65) Prior Publication Data

US 2018/0153390 A1 Jun. 7, 2018

Related U.S. Application Data

(62) Division of application No. 13/991,981, filed as application No. PCT/US2011/063948 on Dec. 8, 2011, now abandoned.
(Continued)

(51) Int. Cl.
*A61B 1/00* (2006.01)
*A61B 1/313* (2006.01)
(Continued)

(52) U.S. Cl.
CPC ...... *A61B 1/00108* (2013.01); *A61B 1/00013* (2013.01); *A61B 1/00016* (2013.01);
(Continued)

(58) Field of Classification Search
CPC ............ A61B 1/00016; A61B 1/00045; A61B 1/00108; A61B 1/3132; A61M 13/003
See application file for complete search history.

(56) References Cited

U.S. PATENT DOCUMENTS 3,812,847 A 5/1974 Moore et al.
4,993,424 A 2/1991 Suszynski et al.
(Continued)

FOREIGN PATENT DOCUMENTS

CN 1695546 A 11/2005
CN 101065049 A 10/2007
(Continued)

OTHER PUBLICATIONS

Chinese Office Action for Application No. CN201710589647.6 dated Jun. 25, 2019.
(Continued)

*Primary Examiner* — Aaron B Fairchild
(74) *Attorney, Agent, or Firm* — Kevin E. West; Advent, LLP

(57) ABSTRACT

A portable laparoscope is disclosed. In implementations, the portable laparoscope includes a housing and an elongated tube coupled to the housing. A lighting source and a camera are disposed proximate to an end of the elongated tube opposite the housing. The camera is configured to capture an image in a viewing area that is illuminated by light provided by the lighting source. The portable laparoscope includes an image display apparatus configured to display the images acquired by the camera and/or to transmit the images to a remote display device. The housing may be configured to hold and position an insufflator.

12 Claims, 12 Drawing Sheets

Related U.S. Application Data

(60) Provisional application No. 61/420,901, filed on Dec. 8, 2010.

(51) Int. Cl.
*A61B 1/05* (2006.01)
*A61B 1/06* (2006.01)
*A61M 13/00* (2006.01)

(52) U.S. Cl.
CPC ...... *A61B 1/00045* (2013.01); *A61B 1/00052* (2013.01); *A61B 1/00183* (2013.01); *A61B 1/05* (2013.01); *A61B 1/0676* (2013.01); *A61B 1/3132* (2013.01); *A61M 13/003* (2013.01)

(56) References Cited

U.S. PATENT DOCUMENTS

| | | | |
|---|---|---|---|
| 5,428,484 | A | 6/1995 | Baker |
| 5,785,644 | A | 7/1998 | Grabover et al. |
| 5,928,137 | A | 7/1999 | Green |
| 6,387,043 | B1 | 5/2002 | Yoon |
| 2005/0080342 | A1 | 4/2005 | Gilreath et al. |
| 2005/0197536 | A1 | 9/2005 | Banik et al. |
| 2005/0222535 | A1* | 10/2005 | Uesugi ............ A61B 1/042 604/26 |
| 2006/0155168 | A1 | 7/2006 | Pease |
| 2006/0217591 | A1 | 9/2006 | Abe |
| 2006/0241348 | A1 | 10/2006 | Kohno |
| 2007/0244363 | A1 | 10/2007 | Sano et al. |
| 2007/0265502 | A1 | 11/2007 | Minosawa et al. |
| 2008/0033450 | A1 | 2/2008 | Bayer et al. |
| 2009/0005636 | A1 | 1/2009 | Pang et al. |
| 2009/0105538 | A1 | 4/2009 | Van Dam et al. |
| 2009/0225159 | A1 | 9/2009 | Schneider |
| 2009/0287060 | A1 | 11/2009 | Pell et al. |
| 2010/0094090 | A1 | 4/2010 | Mejia |
| 2010/0198009 | A1 | 8/2010 | Farr et al. |
| 2011/0009694 | A1 | 1/2011 | Schultz et al. |

FOREIGN PATENT DOCUMENTS

| | | |
|---|---|---|
| CN | 101184429 A | 5/2008 |
| CN | 101208037 A | 6/2008 |
| CN | 201189165 Y | 2/2009 |
| WO | 9942030 A1 | 8/1999 |
| WO | 2009015396 A2 | 1/2009 |
| WO | 2010088135 A2 | 8/2010 |
| WO | 20100123858 A2 | 10/2010 |

OTHER PUBLICATIONS

Examination Report from India Patent Application No. 1701/KOLNP/2013, dated Aug. 27, 2019.
Chinese Office Action for Appln. No. 201710589647.6, dated Jul. 30, 2018.
Office Action for Chinese Application No. 201710589647.6, dated Feb. 3, 2020.
Search Report from Chinese Application No. 201180058958.0 received with Office Action dated Feb. 15, 2015.
Search Report from Chinese Application No. 2011800589580 received with Office Action dated Aug. 13, 2015.
Extended Search Report from European Application No. 118466085 dated Mar. 27, 2015.
European Examination Report from European Application No. 118466085 dated Dec. 2, 2016.
European Examination Report from European Application No. 118466085 dated Aug. 7, 2017.

* cited by examiner

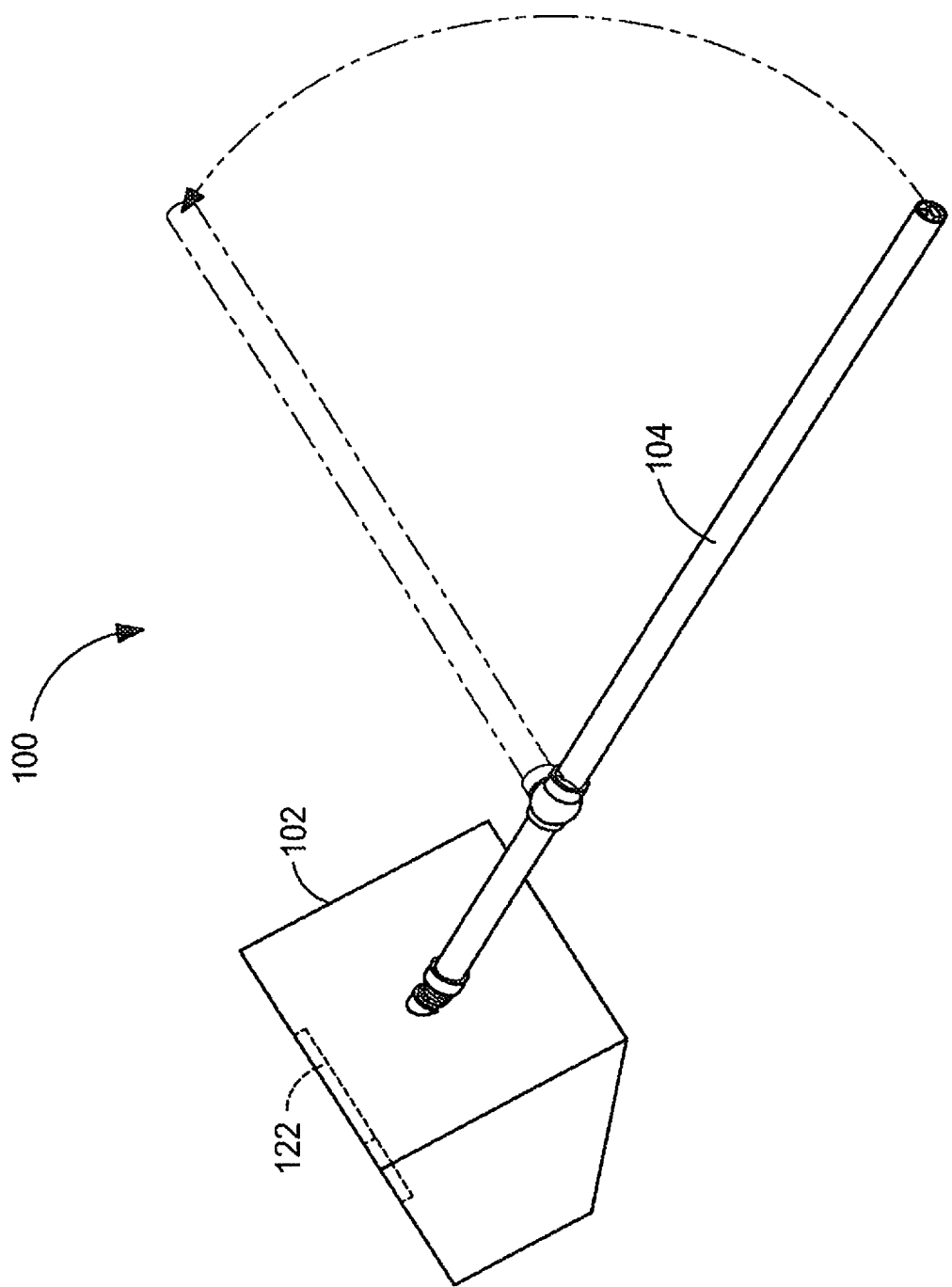

PORTABLE LAPAROSCOPE SYSTEM

BACKGROUND

Medical professionals employ laparoscopes to perform minimally invasive surgery on a patient's abdominal cavity for diagnostic and treatment purposes. Generally, laparoscopes comprise an instrument configured to pass through a small incision (e.g., in the abdominal wall) and capture images (e.g., video) of areas within a patient. The captured images are normally displayed by large monitors that are positioned proximate to the laparoscopic procedure area (e.g., suspended from the ceiling of the operating room around the operating table). During use, laparoscopes require a myriad of associated equipment, such as power sources, insufflators and so on, which are coupled to the laparoscope via a wiring/tube harness, and so forth. Consequently, laparoscopes are confined to use in dedicated surgical environments, such as a laparoscopic operating room in a hospital.

SUMMARY

A portable laparoscope is disclosed. The portable laparoscope is capable of providing laparoscopic imaging functionality to medical personnel in unconventional environments (e.g., environments other than a dedicated laparoscopic operating room, including environments such as but not necessarily limited to: rural areas, combat zones, and so on). In implementations, the portable laparoscope includes a housing and an elongated tube coupled to the housing. A lighting source and an image capture device are disposed proximate to an end of the elongated tube opposite the housing. The image capture device is configured to capture an image in a viewing area that is illuminated by light provided by the lighting source. The portable laparoscope includes an image display apparatus configured to display the images acquired by the image capture device and/or to transmit the images to a remote display device. The portable laparoscope may be configured to position and hold an insufflator.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items. It should be noted that the drawings are not necessarily to scale.

FIG. 4C is a diagrammatic isometric view illustrating a portable laparoscope including a display device configured to articulate to provide multiple viewing angles in accordance with example implementations of the present disclosure.

DETAILED DESCRIPTION

Overview

Figure 1:
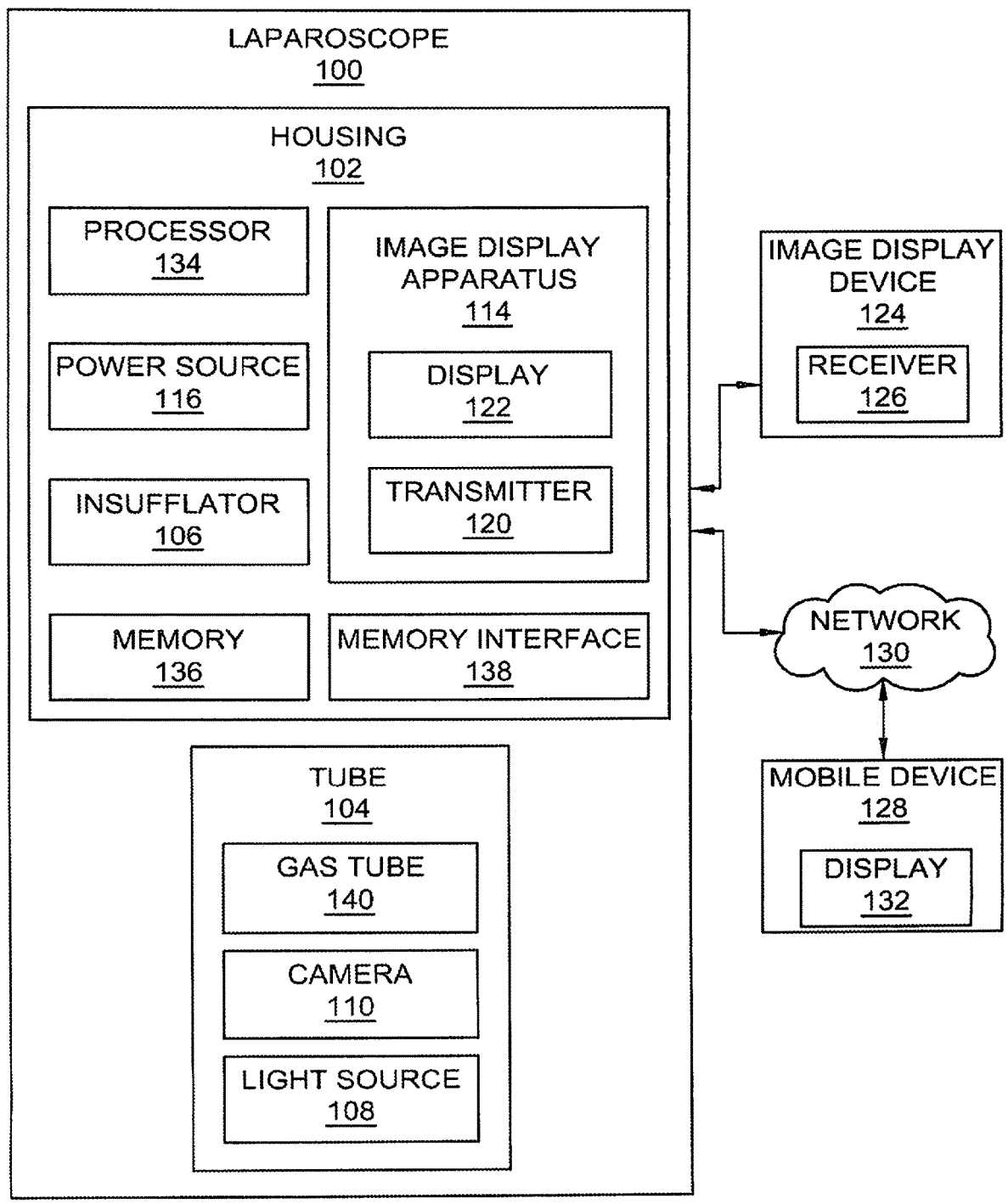
FIG. 1 is a block diagram illustrating an example portable laparoscope in accordance with example implementations of the present disclosure.

Laparoscopes are generally used to perform minimally invasive surgeries. Laparoscopes employ a variety of detached equipment such as power sources, insufflators, monitors, and so on, which are coupled to the laparoscope via a wiring/tube harness, or the like. For example, laparoscopic equipment is generally connected to a bank of large display screens arranged within a dedicated operating room in order to provide a physician with as large and as detailed a view of a patient's internal organs as possible. Consequently, laparoscopes are very expensive, cumbersome and time consuming to set-up. Thus, laparoscopes have been confined to use in dedicated surgical environments such as a laparoscopic operating room in a hospital, surgical center, or the like.

In many instances, access to a dedicated surgical environment can be difficult or even impossible, especially when multiple patients must be evaluated and/or treated in a short span of time, such as during a mass casualty event. For example, in the case of an individual who has been subjected to multiple traumatic injuries, there may be a high risk of internal bleeding. Instant triage evaluation of this type of polytrauma patient in the emergency room itself may be difficult, compounded by the fact that diagnosing internal bleeding is very time sensitive in order to provide effective intervention. Although a technique such as Focused Assessment with Sonography for Trauma (FAST) can provide some information, it lacks the ability to fully visualize internal organs in an ambulatory setting, which can help significantly in triaging patients. Further, in the Intensive Care Unit (ICU), diagnosing the onset of internal bleeding or other internal maladies is often complicated because polytraumatic patients are difficult to move or immobile. Thus, in both triage and ICU settings, imaging devices such as Computed Tomography (CT) devices or Magnetic Resonance Imagining (MRI) devices are not feasible solutions, especially when patients are hemodynamically stable and cannot be moved and such equipment is unavailable. With abdominal trauma, the use of CT with contrast may be preferred. As discussed, neither a triage nor an ICU setting lends itself to CT scanning due to a critical condition of patients, lack of patient mobility, and/or time constraints.

Accordingly, a portable laparoscope is disclosed. In one or more implementations, the portable laparoscope includes a housing and an elongated tube coupled to the housing. The portable laparoscope can be configured to support an insufflator. A lighting source and an image capture device (e.g., a camera) are disposed proximate to an end of the elongated tube opposite the housing. The camera is configured to capture an image in a viewing area that is illuminated by light provided by the lighting source. The portable laparoscope includes an image display apparatus configured to display the images acquired by the camera and/or to transmit the images to a remote display device. In one example, the image display apparatus may comprise a display such as a Liquid Crystal Display (LCD) for displaying captured images and/or captured video of a patient's internals, such as an abdominal cavity, and so forth. In another example, the image display apparatus includes a transmitter disposed in the housing that is configured to transmit images and/or video captured by the camera to a receiver. The receiver is configured to receive the images and/or video for display by a display device communicatively coupled to the receiver.

The portable laparoscope is capable of providing laparoscopic imaging functionality to medical personnel in unconventional environments (e.g., environments other than a dedicated laparoscopic operating room). Thus, the portable laparoscope may be configured to be used in a variety of environments. For example, the portable laparoscope may be used in remote areas, such as, but not necessarily limited to: military field hospitals or rural areas, in a hospital environment outside of the operating room, or in areas where sophisticated and expensive medical equipment is generally not available. Further, the portable laparoscope may be used in applications other than surgical intervention, such as for surgical evaluation outside of an operating room.

The portable laparoscope may be used for determining the presence and/or extent of abdominal trauma. This information can then be used to determine an appropriate course of action in treatment, making conservative management of abdominal injury possible by providing information more accurate than that provided by a CT scan. Further, because portable laparoscopy can provide direct visualization of an abdominal cavity, resolution may not significantly influence diagnostic fidelity. However, using a portable laparoscope for abdominal trauma is provided by way of example only and is not meant to be restrictive of the present disclosure. Thus, a portable laparoscope can also be used for ischemic bowel, which may otherwise be difficult to diagnose, and often frustrates radiographic evaluation. Portable laparoscopy at a bedside in the ICU may dramatically ease diagnosis of ischemic bowel with much higher fidelity. In addition to the triage bay and ICU, portable laparoscopy may also be performed in multiple locations outside of the operating room. For example, most medical clinics have a clean space to perform procedures such as lumbar puncture or colonoscopy. Such rooms may also be utilized for laparoscopic evaluation using a portable laparoscope in accordance with the present disclosure. In the following discussion, an example portable laparoscope is described.

Example Environment

It will be understood that when an element is referred to as being "connected," "coupled," "operatively coupled," and/or "communicatively coupled" to another element, it can be directly connected or coupled to the other element, or intervening elements may be present. In contrast, when an element is referred to as being "directly connected" or "directly coupled" to another element, there are no intervening elements present. Additionally, like numbers refer to like elements throughout. Reference will now be made in detail to the subject matter disclosed, which is illustrated in the accompanying figures.

FIGS. 1 through 6 illustrate an example portable laparoscope 100. As shown, the portable laparoscope 100 includes a housing 102 and an elongated tube 104 coupled to the housing 102. The housing can be configured to support an insufflator 106. A light source 108 and a camera 110 are disposed proximate to a first end 112 of the elongated tube 104 coupled to the housing 102. The housing 102 is also configured to hold image display apparatus 114, that can be configured to display the images acquired by the camera 110 and/or transmit the images to a remote display device. A power source 116 may also be disposed in the housing 102 to provide sufficient operational power to the electronic devices disposed in the portable laparoscope 100 (e.g., light source 108, camera 110, image display apparatus 114, etc.). The housing 102 may be fabricated of a medical grade material such as titanium. However, titanium is provided by way of example only, and is not meant to be restrictive of the disclosure. Thus, other materials medical grade materials may be used to construct the housing 102, the elongated tube 104, and so forth.

The elongated tube 104 may be configured in a variety of ways. As shown, the elongated tube 104 includes a first end 112 and a second end 118. The first end 112 is defined by the end of the elongated tube 104 distal from the housing 102. In implementations, a light source 108 and a camera 110 are disposed of the elongated tube 104 proximate to the first end 112. In some implementations, the light source 108 and/or the camera 110 can be disposed of the elongated tube 104 proximate to the second end 118. In this type of configuration, lenses, fiber optic cables, and the like can be used to direct light to and from the light source 108 and/or the camera 110 along the length of the elongated tube 104. The light source 108 and/or the camera 110 can also be positioned within the housing 102. A window formed of generally transparent material is disposed at the first end 112 to provide a protective cover for the light source 108 and the camera 110 and other equipment within the elongated tube 104. In embodiments, the generally transparent material may be comprised of quartz, or the like.

The second end 118 of the elongated tube 104 is coupled to the housing 102 using, for example, a threaded fitting. The fitting can be used to provide articulation between the housing 102 and the elongated tube 104. For example, the fitting can be implemented as a joint. The second end 118 may also be welded to or fastened to the threaded fitting. In an implementation, the elongated tube 104 may comprise an approximately fourteen inch (14") (355.6 millimeters) long tube that is ten millimeters (10 mm) (0.39 inches) in diameter. The elongated tube 104 may also be comprised of a rigid material (e.g., titanium), a flexible material (e.g., medical nylon), or other medical grade materials. In some implementations, the elongated tube 104 can be configured to extend and retract. For example, the elongated tube 104 can be configured to telescope, and/or to retract into the housing 102.

The insufflator 106 may be used to supply a gas (e.g., $CO_2$) to the abdominal cavity to lift abdominal integument from the internal organs proximate to the first end 112 of the elongated tube 104. The insufflator 106 may be implemented in a variety of ways. For example, the insufflator may comprise a cartridge-based insufflator, a gas cylinder-based insufflator, an infusion balloon-based insufflator, or other medically suitable portable insufflators. The insufflator 106 can be disposed or housed within the housing 102.

The light source 108 may assume a variety of configurations. For example, the light source 108 may be comprised of a light emitting diode (LED), a laser diode, quantum dots, multiple light emitting diodes, multiple laser diodes, or the like. In an implementation, the light source 108 is disposed at the first end 112 proximate to a camera 110, and the power source 116 is coupled (e.g., wired configuration, etc.) to the light source 108 to provide sufficient operational power to the light source 108. When the portable laparoscope 100 is in use, the light source 108 is configured to emit a light to illuminate an area within a field of view of the camera 110.

Figure 4A:
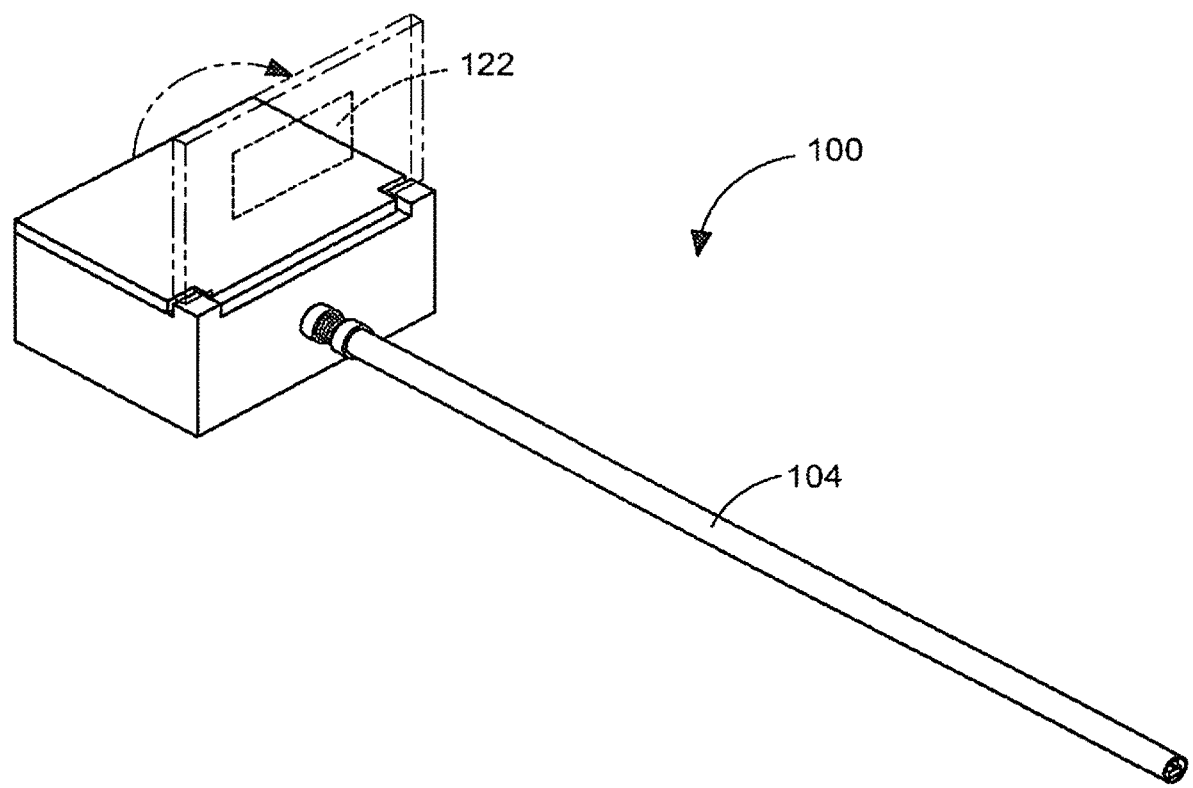
FIG. 4A is a diagrammatic isometric view illustrating a portable laparoscope configured with a flip screen display device in accordance with example implementations of the present disclosure.
Figure 4B:
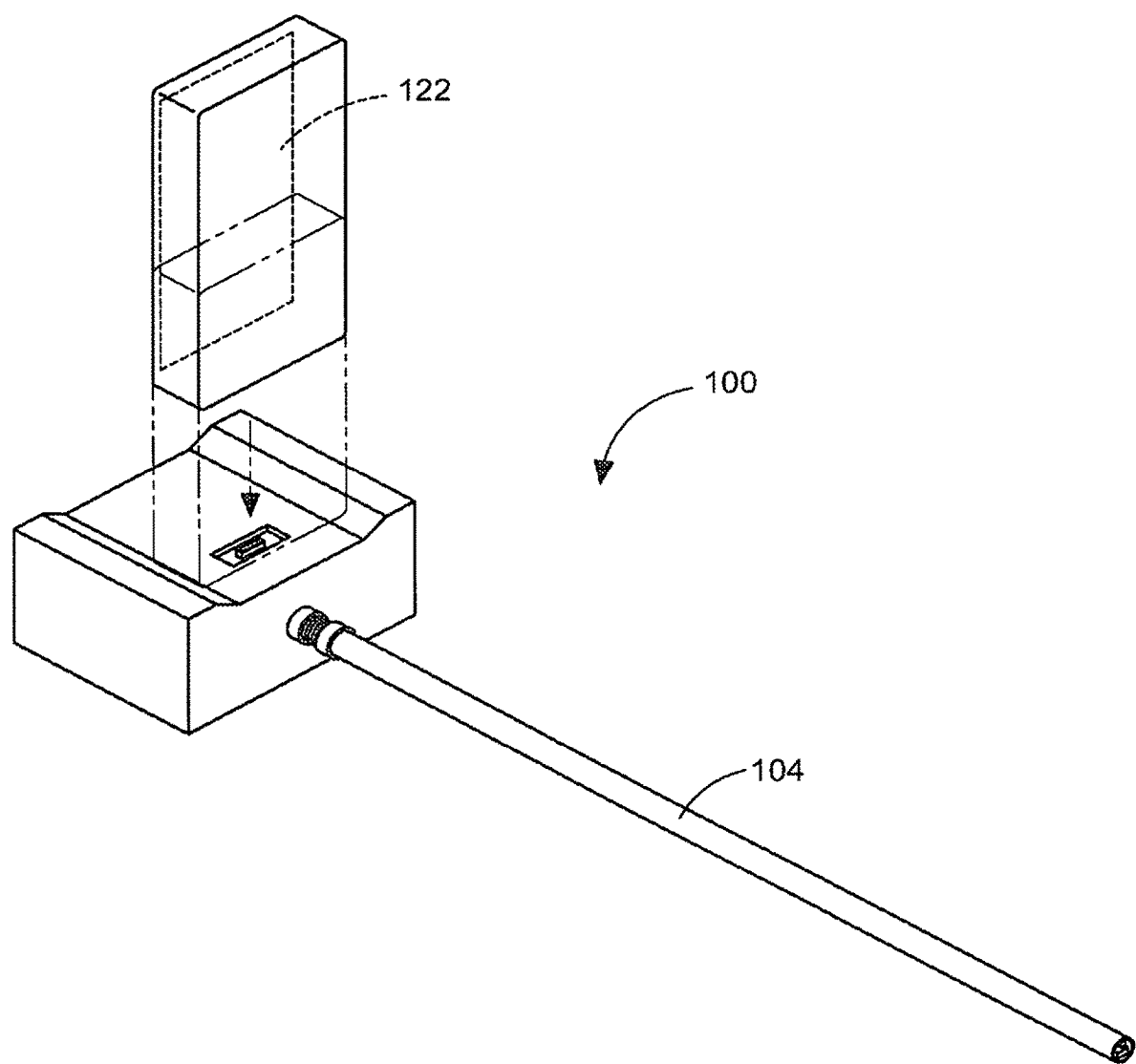
FIG. 4B is a diagrammatic isometric view illustrating a portable laparoscope configured to employ a mobile device for display of images in accordance with example implementations of the present disclosure.
Figure 4D:
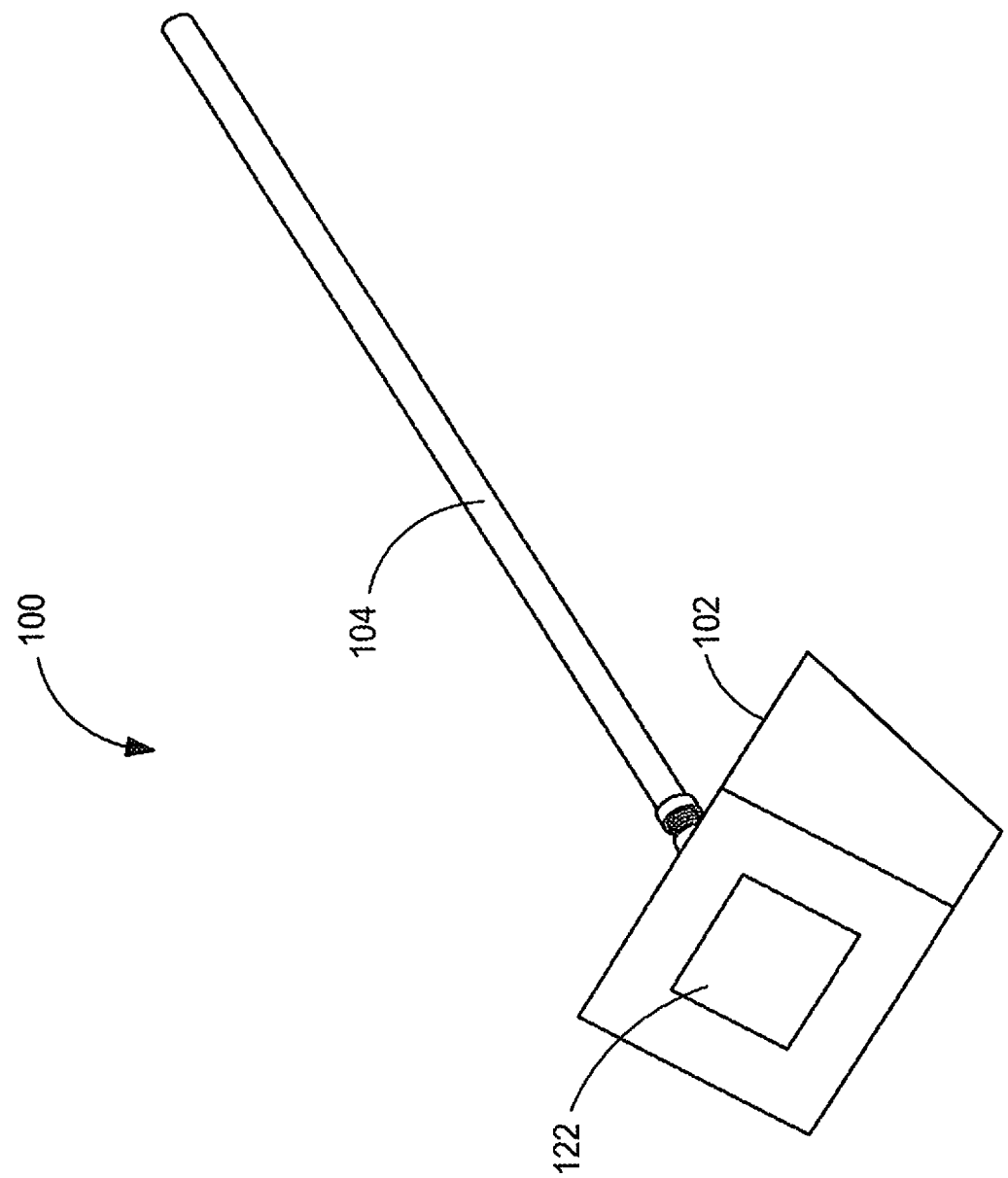
FIG. 4D is a diagrammatic isometric view illustrating a portable laparoscope including a fixed display device in accordance with example implementations of the present disclosure.
Figure 4E:
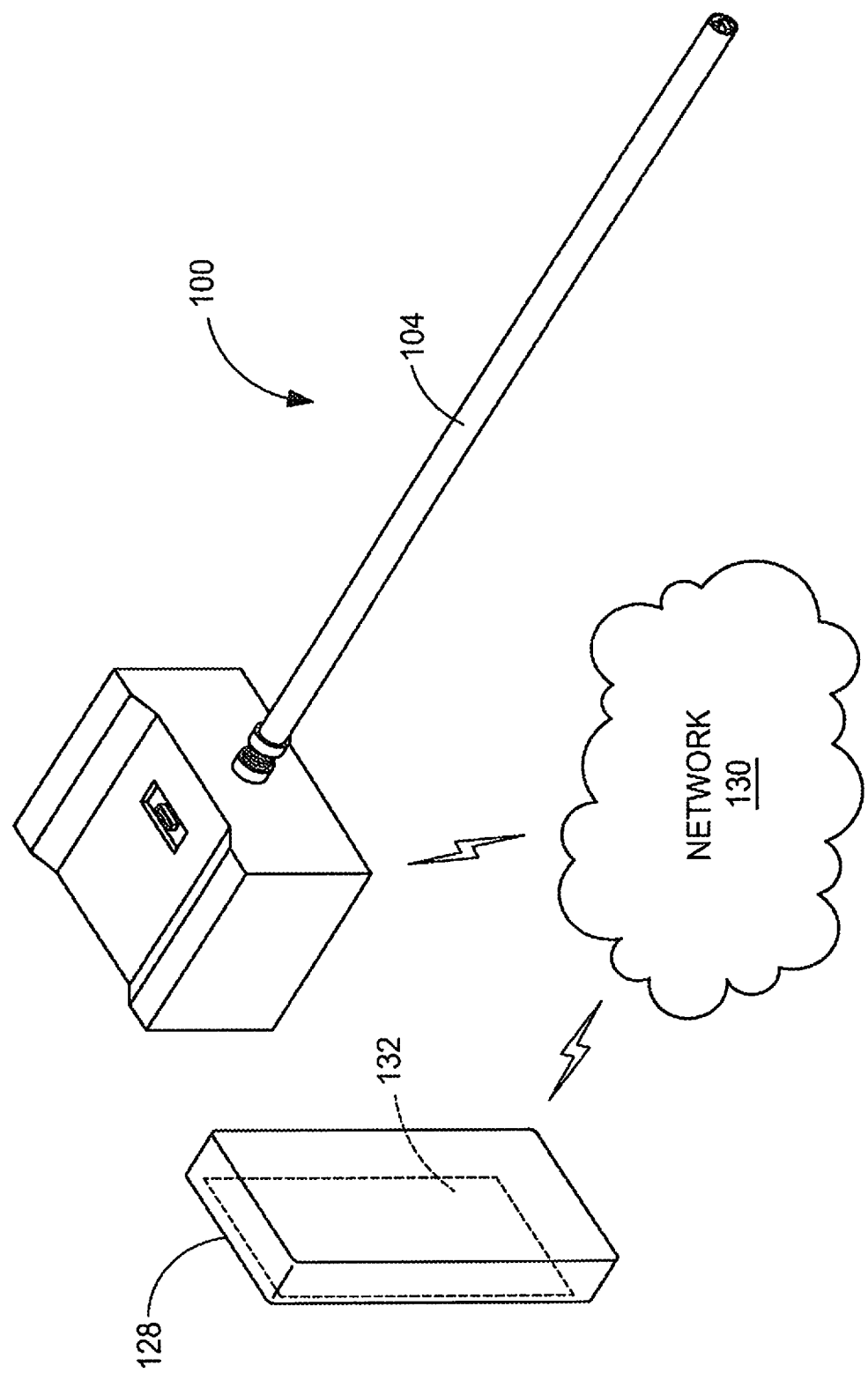
FIG. 4E is a diagrammatic isometric view illustrating a portable laparoscope coupled with a detachable display device in accordance with example implementations of the present disclosure.
Figure 4F:
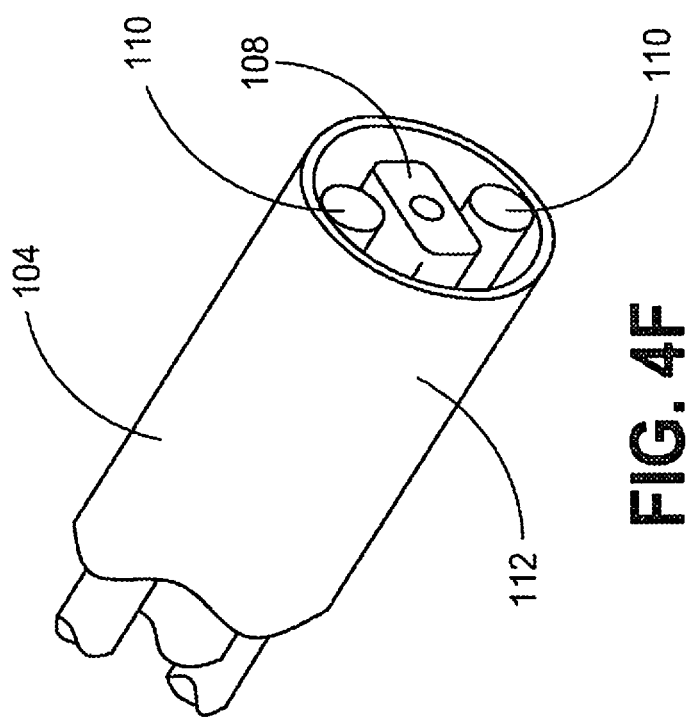
FIG. 4F is a partial diagrammatic isometric view illustrating an end of an elongated tube of a portable laparoscope, where a light source and a camera array is disposed at the end of the elongated tube in accordance with example implementations of the present disclosure.

The camera 110 may be configured in a variety of ways. The camera 110 may, for example, be comprised of: a pin hole camera, a charge coupled device (CCD) camera, a fiber optic coupled camera, a video camera, and so forth. The camera 110 is configured to capture an image in the camera's field of view. The camera 110 is disposed proximate to the first end 112 and coupled to the power source 116. In an implementation, the camera 110 may be part of a group of multiple cameras 110 disposed proximate to the first end 112 and coupled to the power source 116. As illustrated in FIG. 4F, multiple cameras 110 can be disposed at different locations of the first end 112 to capture multiple images from different angles. The multiple cameras 110 may also be arranged in such a configuration that provides a stereoscopic view of the captured images when displayed.

The camera 110 is configured to communicate with image display apparatus 114. For example, one or more cameras 110 may be communicatively coupled to an electronic device (e.g. a display 122, etc.) via a wired configuration, a fiber optic communication, a transmitter/receiver link, or the like. In an implementation, the camera 110 is configured to transfer the captured image data to an image display apparatus 122 disposed of the housing 102.

The image display apparatus 114 may assume a wide variety of configurations, as illustrated in FIGS. 4A through 4E. The image display apparatus 114 is configured to display images captured by cameras 110 and/or to transmit the images to a remote display device. For example, the image display apparatus 114 may include, but is not necessarily limited to: a transmitter 120 configured to transmit captured images; a display 122, such as a liquid crystal display (LCD) device or a projection device; and so forth. The camera 110 and the image display apparatus 114 are communicatively coupled together via a wired configuration, a wireless configuration, a fiber optic configuration, or the like.

In an implementation, the image display apparatus 114 may be configured as a display 122 disposed of (e.g., housed within) the housing 102. For example, the display 122 may be a flip-screen display device, as illustrated in FIG. 4A. As shown, the flip-screen display device may be configured to pivot from a substantially folded position for transportation and storage to a substantially upright position for viewing purposes. In another example, the display 122 may be coupled to the elongated tube 104 (shown in FIGS. 4C, 4D, and 4G). For instance, the housing 102 may include an aperture to allow viewing of the display portion of the display 122. It is contemplated that the display 122 may be a display device of varying dimensions. For example, the display 122 may be comprised of an approximately 2.5 inch (6.35 centimeter) diagonal LCD device, an approximately 5.8 inch (14.73 centimeters) diagonal LCD device, and so forth. The display 122 may present the captured image(s) as individual images for a predetermined amount of time. The captured images may also be presented as a sequence of images (e.g., video). In another implementation, the display 122 may comprise a projection device, such as a liquid crystal display (LCD) projector, or the like. The housing 102 may be configured to house the projection device. In an implementation, the projection device is configured to project images as a virtual screen to a viewing area. The viewing area may include, but is not necessarily limited to: a projection screen, a wall, or another projection viewing medium.

As illustrated in FIG. 1, the image display apparatus 114 may comprise a transmitter 120. The transmitter 120 may be configured in a variety of ways. For example, the transmitter 120 may be a Radio Frequency (RF) transmitter configured to transmit one or more images captured by camera 110 via a RF network (e.g., Bluetooth, Wi-Fi, etc.). In another example, the transmitter I2C may comprise a laser diode configured to transmit one or more image(s) via a free-space optical network. The transmitter 120 may be housed within the housing 102 and coupled to power source 116.

The transmitter 120 can be configured to transmit one or more captured image(s) to a remote display device. The remote display device may be configured in a variety of ways. In an implementation, the remote display device may be comprised of an image display device 124. The image display device 124 may be a monitor (e.g., LCD device, High Definition (HD) display device, etc.) communicatively coupled (e.g., wired configuration, wireless configuration, etc.) to a receiver 126. A receiver 126 is configured to receive the one or more image(s) transmitted by the transmitter 120 and to provide the one or more image(s) to the image display device 124. The receiver 126 may be implemented in a number of ways. For example, the receiver 126 may be a RF receiver configured to receive images from a RF transmitter. In another example, the receiver 126 may be an avalanche photodiode configured to receive images from a laser diode.

In an implementation, the receiver 126 is configured to receive the image(s) transmitted by the transmitter 120 and to furnish the images to the image display device 124 via a wired configuration. For example, the receiver 126 and image display device 124 may be located in a separate area (e.g., building, room, etc.) from the transmitter 120 and portable laparoscope 100.

It is contemplated that a mobile device 128 may be used to view the image(s) furnished by camera 110. In an implementation, mobile device 128 may be coupled to elongated tube 104 via a wired configuration as illustrated in FIG. 4B. In another implementation, the transmitter 120 may be configured to transmit the captured image(s) to a detachable mobile device 128 via a network 130 as illustrated in FIG. 4E. The mobile device 128 may be configured in a variety of ways. For instance, the mobile device 128 may be configured as a mobile phone, a smart phone, a laptop computing device, and so forth. The mobile device 128 may include a display 132. In an implementation, the display 132 may be integral with the mobile device 128. In another implementation, the display 132 may be coupled to the mobile device 128 via a wired configuration. For example, the transmitter 120 may transmit the captured image(s) to a mobile phone 128 via the network 130. The mobile phone 128 furnishes the captured image(s) to the display 132 for display. In another example, the transmitter 120 may transmit the captured image(s) to a laptop computer 128 via the network 130. The laptop 128 furnishes the captured image(s) to the display 132 for display.

The network 130 is representative of a variety of different communication pathways and network connections that may be employed, individually or in combinations, to communicate among the components of the portable laparoscope 100. Further, network 130 is representative of a variety of different types of networks and connections that are contemplated including, but not necessarily limited to: the Internet; an intranet; a satellite network; a cellular network; a mobile data network; wired and/or wireless connections; and so forth.

Examples of wireless networks include, but are not necessarily limited to: a free-space optical transmission network, a wireless LED network, as well as networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; and so on. Wired communications are also contemplated such as through universal serial bus (USB), Ethernet, serial connections, and so forth. As illustrated in FIG. 1, the portable laparoscope 100 includes a power source 116. In an implementation, the power source 116 may comprise a battery that is configured to provide sufficient operational power to the various electronic components associated with or coupled to the portable laparoscope 100. For instance, in an implementation, the battery provides sufficient operational power to operate the image display apparatus 114, the insufflator 106, the camera 110, and the light source 108. It is contemplated that sufficient operational power may be defined as each electronic device powered by the battery receiving enough power to be fully operational according to the specifications of each device for a definite amount of time.

In FIG. 1, the laparoscope 100 is depicted as including a processor 134 and a memory 136. The processor 134 provides processing functionality for the portable laparoscope 100 and may include any number of processors, microcontrollers, or other processing systems and resident or external memory for storing data and other information accessed or generated by portable laparoscope 100. The processor 134 is configured to execute one or more software program(s). The processor 134 is not limited by the materials from which it is formed or the processing mechanisms employed therein and, as such, may be implemented via semiconductor(s) and/or transistors (e.g., electronic Integrated Circuits (ICs)), and so forth.

The memory 136 is an example of tangible computer-readable media that provides storage functionality to store various data associated with the operation of the portable laparoscope 100, such as the software program and code segments mentioned above, or other data to instruct the processor 134 and other elements of the portable laparoscope 100 to perform the steps described herein. Although a single memory 136 is shown, a wide variety of types and combinations of memory may be employed. The memory 136 may be integral with the processor 134, stand-alone memory, or a combination of both. The memory may include, for example, removable and non-removable memory elements such as Random Access Memory (RAM), Read Only Memory (ROM), Flash memory (e.g., an SD Card, a mini-SD card, a micro-SD Card), magnetic memory, optical memory, USB memory devices, and so forth.

As depicted in FIG. 1, the housing 102 includes a memory interface 138. The memory interface 138 provides removable storage functionality to portable laparoscope 100. For instance, the memory interface 138 is configured to detect when a removable memory element has been positioned or inserted into memory interface 138. The memory interface 138 is configured to receive the image(s) and/or the video from the camera 110 and furnish the image(s) and/or the video to the removable memory element for storage. The image(s) may be transferred via a protocol implemented in software, hardware, and/or firmware. The removable memory elements may include, but are not necessarily limited to: SD Cards, mini-SD cards, micro-SD Cards, USB drives, or the like. In this configuration, processor 134 may be housed in the housing 102 as a standalone processor, a processor integral with the camera 110, or a processor integral with the memory interface 138. The processor 134 may provide processing functionality to the portable laparoscope 100, the camera 110, and/or the memory interface 138.

Figure 2:
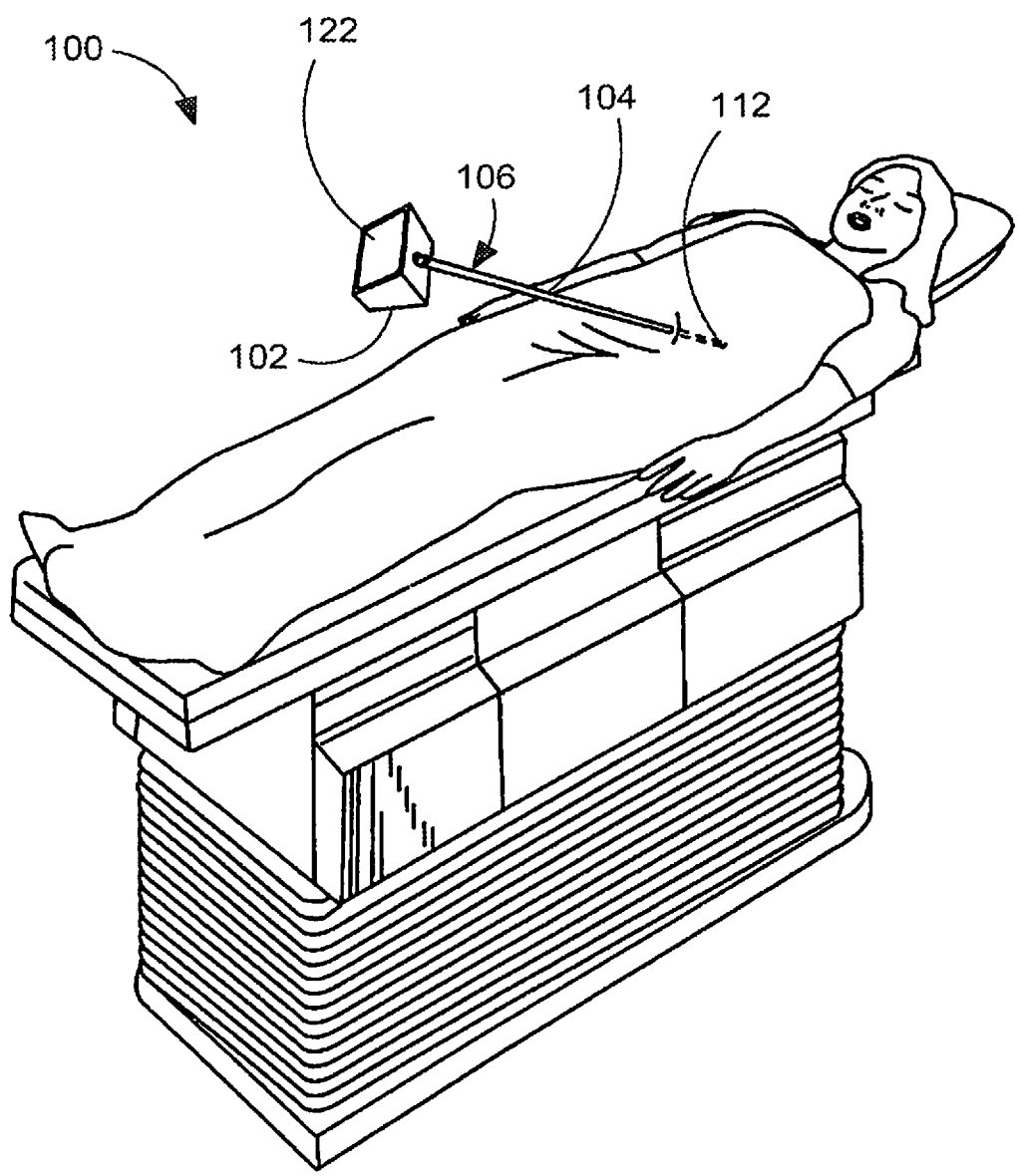
FIG. 2 is a diagrammatic isometric view illustrating a portable laparoscope used in a non-dedicated surgical environment in accordance with example implementations of the present disclosure.
Figure 3:
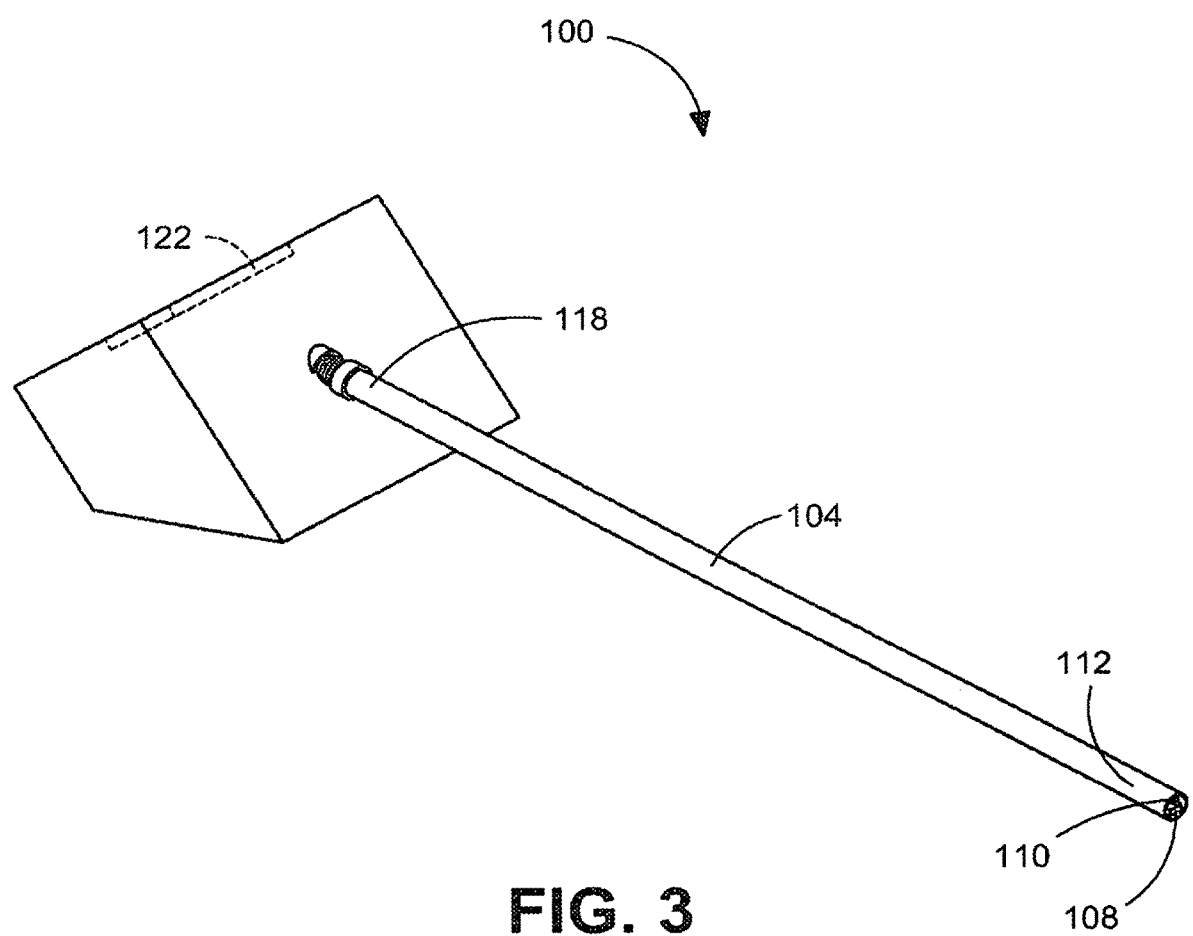
FIG. 3 is a diagrammatic isometric view of the portable laparoscope illustrated in FIG. 2, where a light source and a camera are disposed proximate to an end of an elongated tube of the portable laparoscope.
Figure 4G:
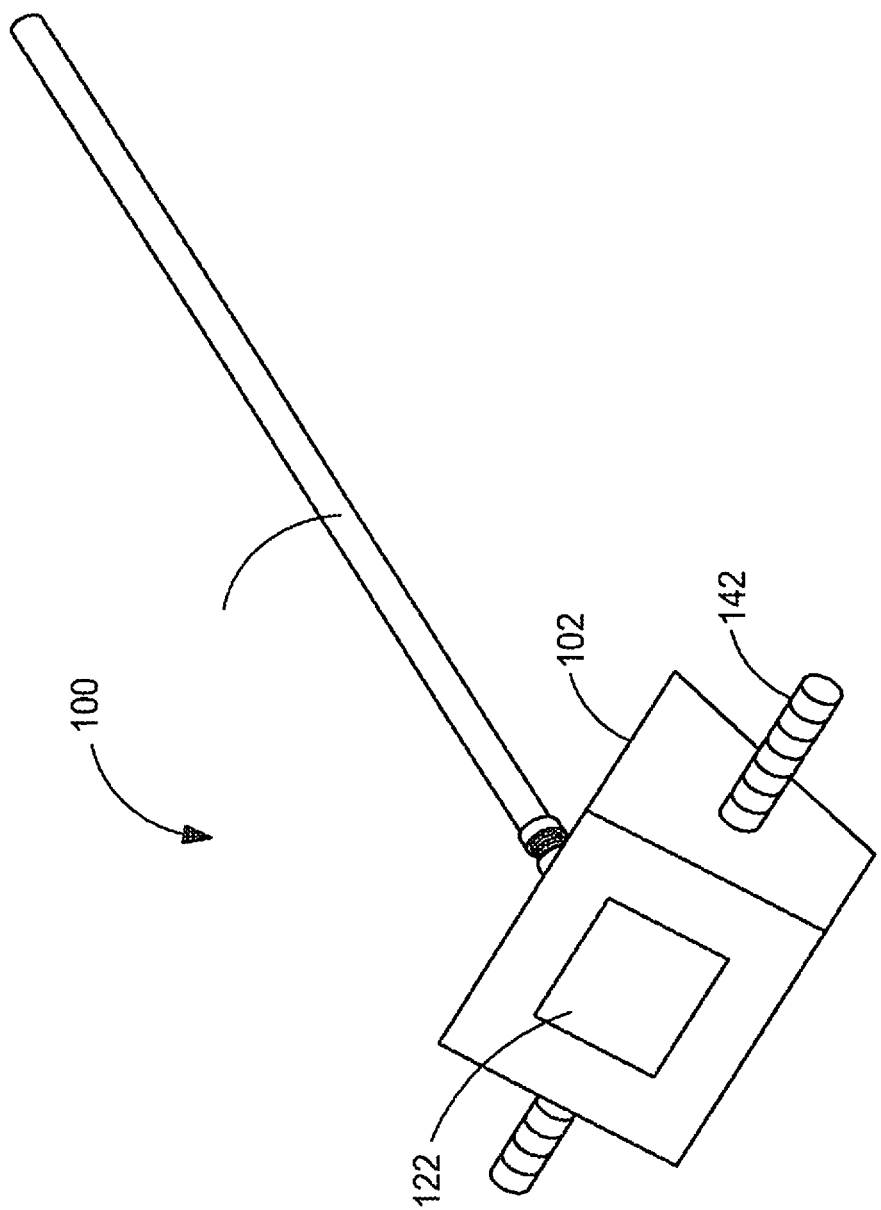
FIG. 4G is a diagrammatic view illustrating a portable laparoscope including a housing configured with a display device and a handle to assist with operating the portable laparoscope in accordance with example implementations of the present disclosure.

FIGS. 2 and 3 illustrate example implementations of portable laparoscopes in accordance with the present disclosure. FIG. 2 depicts a portable laparoscope 100 used in a non-dedicated surgical environment. For instance, medical personnel (not shown) may use laparoscope 100 to perform a laparoscopic procedure on a patient. Medical personnel may insert end 112 through an incision made in patient. As shown in FIG. 3, end 112 includes light source 108 and camera 110. As described above, the light source will provide illumination to the area within the camera's 110 field of view. The camera 110 furnishes one or more image (s) to the image display apparatus 114 (depicted as display 122 in FIGS. 2 and 3) for medical personnel to view. In another implementation, as illustrated in FIG. 4C, portable laparoscope 100 may be manipulated by medical personnel to provide further camera 110 views and so forth. Moreover, portable laparoscope 100 may implemented with ergonomic designs. For instance, as illustrated in FIG. 4G, a handle 142 may be coupled to display 122.

Figure 5:
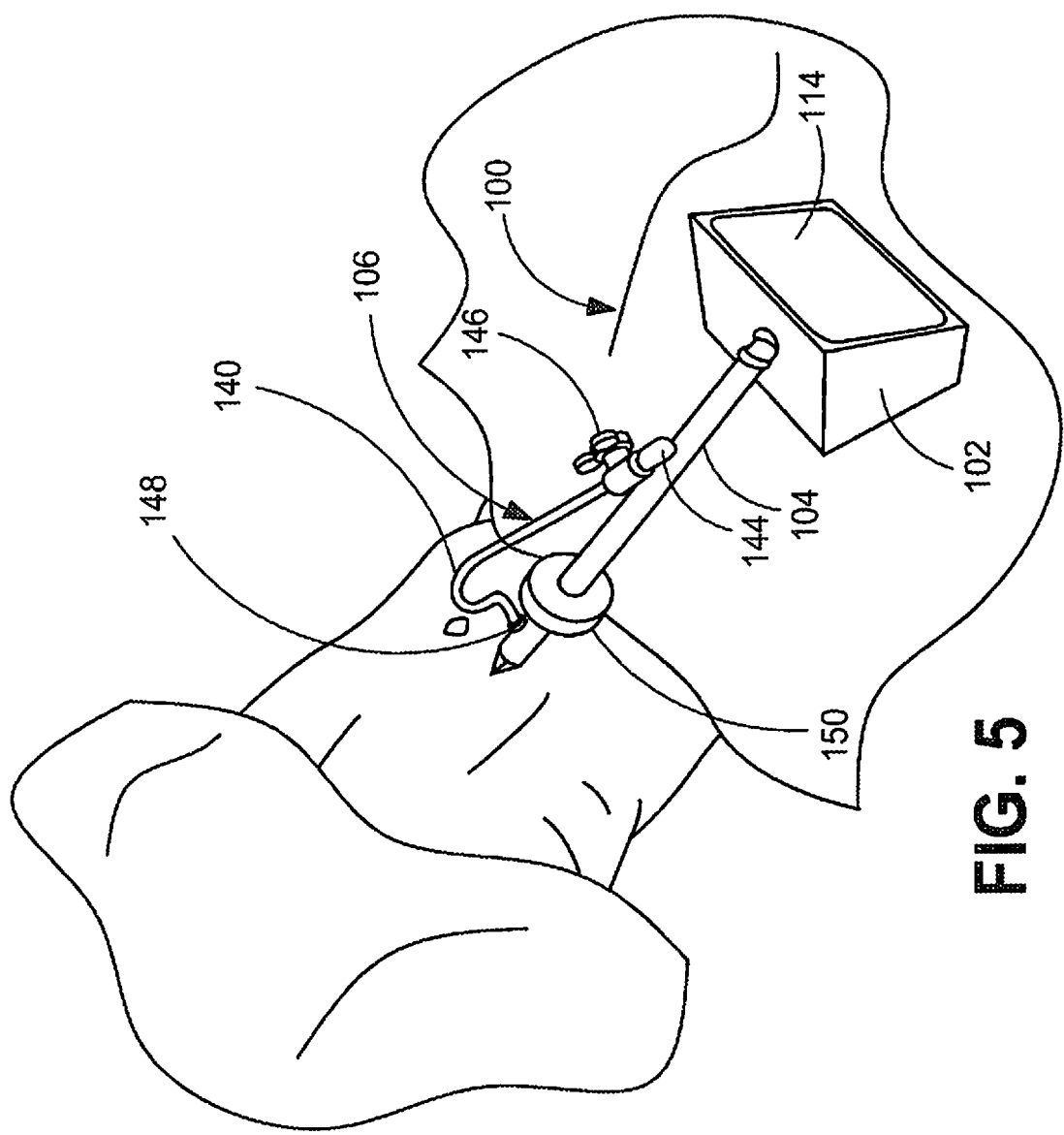
FIG. 5 is a diagrammatic isometric view of a portable laparoscope as used in a surgical environment, where the portable laparoscope includes a gas cartridge, a trocar-hookup, and a trocar in accordance with example implementations of the present disclosure.
Figure 6:
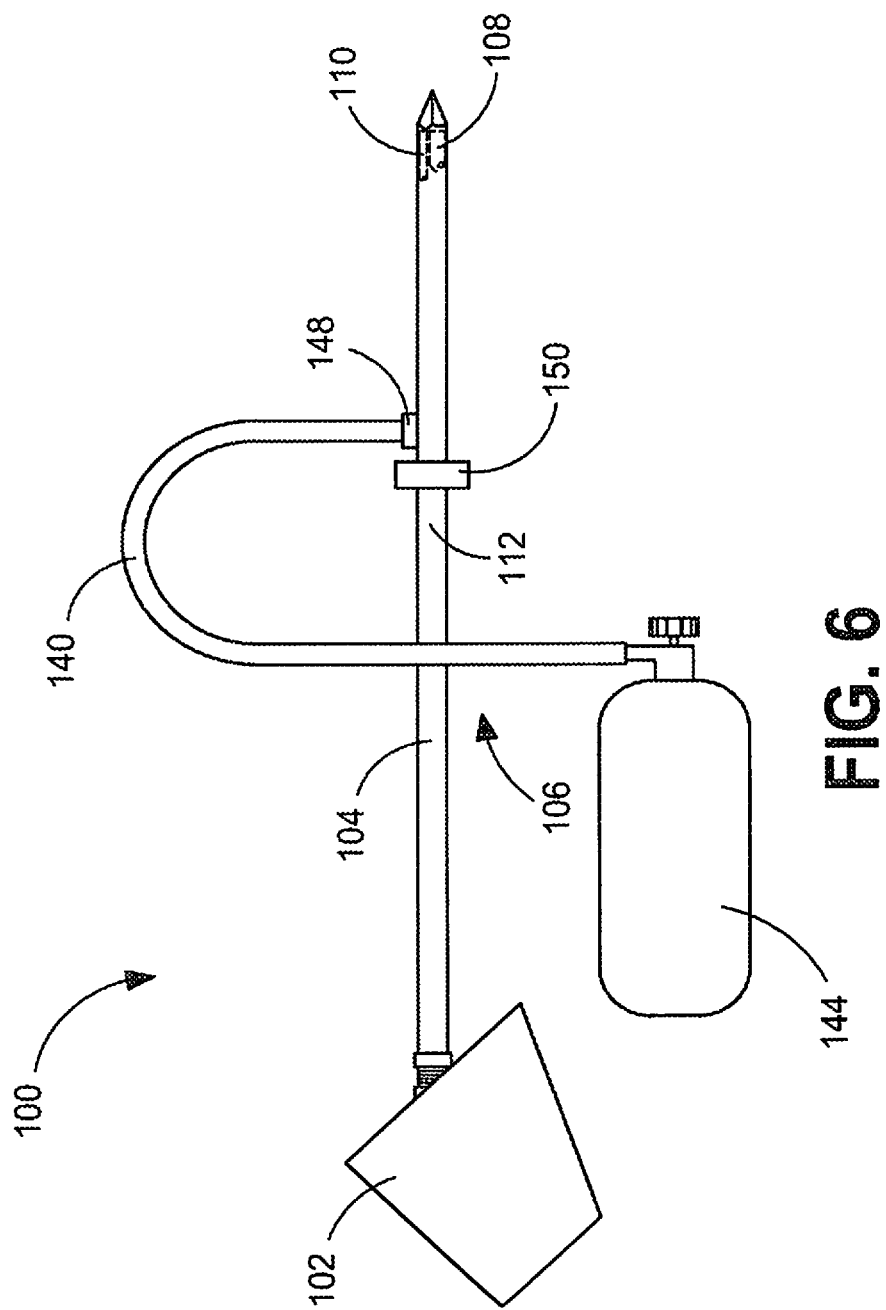
FIG. 6 is a diagrammatic side elevation view of the portable laparoscope illustrated in FIG. 5.

Referring now to FIGS. 5 and 6, the insufflator 106 comprises a portable gas supply 144 coupled to a gas tube 140. The portable gas supply 144 may comprise a portable gas cartridge, a portable gas tank, or the like. A gas regulator 146 is disposed between the portable gas supply 144 and the gas tube 140. The gas regulator 146 is configured to interface with the portable gas supply 144 and to regulate the gas flow released into the gas tube 140 from the portable gas supply 144. In an implementation, the gas regulator 146 may be comprised of a high pressure gas regulator or the like. For example, a high pressure gas regulator may include a FISHERBRAND Multistage Cylinder Regulator, or the like. In an implementation, the gas regulator 146 may be configured to reduce the flow rate of the gas to low variable pressures. In a further implementation, the gas regulator 146 may be coupled, or connected, to a flow meter (not shown) to monitor the flow rate of the insufflator 106. The flow meter may comprise a Smith Flowmeter Regulator, or the like. In one implementation, the gas tube 140 may be disposed, or housed, within the elongated tube 104. In another implementation, the gas tube 140 may be a stand-alone gas tube 140.

In an implementation, as illustrated in FIGS. 5 and 6, the laparoscope 100 may also include a trocar hook-up 148 and a trocar 150. The trocar hook-up 148 provides an interface with the gas tube 140 proximate to the first end 112 of the elongated tube 104. The trocar 150 is configured to make an incision in a patient and is also coupled proximate to the elongated tube 104 and the trocar hook-up 148. Once an incision has been created, the first end 112 of the elongated tube 104 may then be inserted through the incision to allow the camera 110 to provide imagery of the body cavity. It is contemplated that the trocar 150 may be any trocar known in the art and may be interchangeable with other types of trocars. In a further implementation, as illustrated in FIG. 6, the light source 108 and the camera 110 may be disposed proximate to the trocar 150. For instance, the trocar 150 may include the light source 108 and the camera 110 and provide illumination functionality and image capture functionality once the trocar 150 has been inserted through the incision in the patient.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A portable laparoscope system comprising:
    a housing;
    a flexible elongated tube comprising a first end and a second end, the first end of the elongated tube terminating with a window and the second end of the elongated tube coupled to the housing, the elongated tube configured for at least partial insertion into a body cavity, the elongated tube having an outside diameter of ten millimeters (10 mm) or less for insertion through a trocar;
    an image capture device entirely disposed at the first end of the elongated tube, the image capture device configured to capture an image within a field of view of the image capture device, the image capture device including at least one of a pin hole camera, a charge coupled device camera, or a video camera;
    a light source disposed at the first end of the elongated tube, the light source configured to emit a light proximate to an area within the field of view of the image capture device;
    an insufflator configured to provide a gas for inflating a body cavity into which the elongated tube is inserted, the insufflator including a portable gas supply, a gas tube for transporting gas from the portable gas supply to the trocar, a trocar hook-up for the gas tube to interface with the trocar and supply gas from the portable gas supply for inflating the body cavity through the trocar, and a gas regulator disposed between the portable gas supply and the gas tube to regulate the flow rate of the gas to a variable pressure;
    a flow meter to monitor the flow rate of the gas; and
    an image display apparatus mounted to the housing and coupled with the image capture device via a wired connection through the elongated tube, the image display apparatus for displaying an image of a body cavity captured by the image capture device and transmitted to the image display apparatus via the wired connection.

2. The portable laparoscope system as recited in claim 1, wherein the image display apparatus comprises a transmitter communicatively coupled to the image capture device, and an image display device removable from the image display apparatus, the image display device having a receiver, wherein the transmitter is configured to transmit the image to the receiver for display by the image display device.

3. The portable laparoscope system as recited in claim 2, wherein the transmitter is configured to transmit the image via a wireless network.

4. The portable laparoscope system as recited in claim 3, wherein the transmitter is configured to transmit the image via a wireless network conforming to 802.11 standards.

5. The portable laparoscope system as recited in claim 4, wherein the wireless network comprises a free-space optical transmission network.

6. The portable laparoscope system as recited in claim 2, wherein the image display device comprises a projection device.

7. The portable laparoscope system as recited in claim 2, wherein the image display device comprises a liquid crystal display device.

8. The portable laparoscope system as recited in claim 1, further comprises a battery.

9. The portable laparoscope system as recited in claim 1, further comprising the trocar.

10. The portable laparoscope system as recited in claim 1, wherein the insufflator is disposed in the housing.

11. The portable laparoscope system as recited in claim 1, further comprising:
    a memory interface disposed of the housing, the memory interface configured to receive a removable memory element.

12. The portable laparoscope system as recited in claim 1, wherein the portable gas supply comprises a gas cylinder, and the gas regulator comprises a multistage cylinder regulator.

* * * * *